(12) United States Patent
Johnson et al.

(10) Patent No.: US 6,679,093 B2
(45) Date of Patent: Jan. 20, 2004

(54) METHOD OF CALIBRATION USING ANALYTICAL APPARATUS FOR MEASUREMENT OF LOW CONCENTRATION CONSTITUENT

(75) Inventors: John E. Johnson, Lansdale, PA (US); Mark Steinert, Shillington, PA (US)

(73) Assignee: JMIC, Inc., Shillington, PA (US)

(*) Notice: Subject to any disclaimer, the term of this patent is extended or adjusted under 35 U.S.C. 154(b) by 0 days.

(21) Appl. No.: 10/272,961

(22) Filed: Oct. 17, 2002

(65) Prior Publication Data

US 2003/0037589 A1 Feb. 27, 2003

Related U.S. Application Data

(62) Division of application No. 09/791,242, filed on Feb. 23, 2001, now Pat. No. 6,526,811.
(60) Provisional application No. 60/184,399, filed on Feb. 23, 2000.

(51) Int. Cl.[7] .................................................. G01N 1/00
(52) U.S. Cl. ....................................................... 73/1.02
(58) Field of Search ............................ 73/61.52, 61.55, 73/64.56, 863, 863.21, 863.23, 863.72, 863.73, 864.83; 422/82.01–82.03, 68.1; 210/656, 660, 662, 681

(56) References Cited

U.S. PATENT DOCUMENTS

| | | |
|---|---|---|
| 4,766,550 A | 8/1988 | Byers et al. |
| 4,981,804 A | 1/1991 | Hanaoka et al. |
| 4,991,428 A | 2/1991 | Heyde |
| 5,597,481 A | 1/1997 | Stillian et al. |
| 5,908,556 A | 6/1999 | Cavotta et al. |

Primary Examiner—Robert Raevis
(74) Attorney, Agent, or Firm—Akin Gump Strauss Hauer & Feld, L.L.P.

(57) ABSTRACT

An analytical apparatus for measuring a low concentration of a constituent in a stream at a parts per billion level is provided. The apparatus comprises a sample loop having a predetermined volume for receiving a sample from the stream, a purifier for producing substantially pure carrier liquid from a sample of the stream, a first and a second multi-path valve, a preconcentrator column for absorbing and increasing the concentration of the low concentration constituent, an eluent, and a detector. In one embodiment, the apparatus is an ion chromatograph and may be used to analyze ions at concentrations as low as about 1 to about 500 parts per trillion. A method for analyzing a stream for a low concentration constituent present in a stream at a parts per billion level is also provided. The invention also includes methods for single- and multi-point calibration of a detector in an analytical apparatus for measuring a low concentration of a constituent in a stream at a parts per billion level.

20 Claims, 9 Drawing Sheets

I.C. Flow Diagram

Figure 1
I.C. Flow Diagram

Fig. 2
Filling Sample Loop

Fig. 3
Inject Sample
onto Preconcentrator

Fig. 4
Inject Preconcentrator Onto Anion Column

Fig. 5
Inject Standard Loop

Fig. 6
Load Preconcentrator
With Standard Using
Purified Carrier

Fig. 7
Flush Sample Loop While Loading Preconcentrator With Standard

Fig. 8
Load Grab Sample

Fig. 9
Inject Grab Sample

METHOD OF CALIBRATION USING ANALYTICAL APPARATUS FOR MEASUREMENT OF LOW CONCENTRATION CONSTITUENT

CROSS-REFERENCE TO RELATED APPLICATIONS

This application is a divisional of U.S. patent application Ser. No. 09/791,242, filed Feb. 23, 2001, now U.S. Pat. No. 6,526,811. This application claims the benefit of provisional application No. 60/184,399 filed Feb. 23, 2000.

BACKGROUND OF THE INVENTION

This invention pertains to measurement of contaminants or constituents in a sample, and more particularly to measurement of constituents in a sample in which the constituents are in the range of one part per billion (ppb) or less.

Measurement of constituents in a sample at levels of less than or equal to 1 ppb continues to be a challenge, particularly in the part per trillion (ppt) range. For example, ion chromatography can be used to measure anions and cations in a sample, such as in a sample of water. However, current technology for ion chromatography detectors limit sample measurement for ions to about 50 ppb or greater. Higher purity measurements are attainable with preconcentration, but the validity of the results can be affected by the calibration techniques used.

Prior art systems utilize suppression to reduce the background level of conductivity at the detector and preconcentration to collect a large volume of sample. Both techniques enhance response, and in combination, are used to achieve the lowest levels of detection.

Calibration of these systems for measurement at ppt levels is achieved by several methods. One method involves the injection of a standard much more concentrated than the samples of interest, and subsequent extrapolation of the calibration curves down to ppt levels. This process may introduce an error in the calibration, and small errors in the calibration produce large errors at the ppt level. In another method of calibration, a small volume of concentrated standard is injected into the sample stream, eliminating errors caused by extrapolation. However, this method may be susceptible to errors in measurement of the injected volume and the diluent volume, and an error in the volume or flow may cause an error in calibration.

Current requirements for advanced combustion turbines allow the use of steam to provide cooling for a turbine transition section rather than air, which was previously used. Steam has a significantly higher heat transfer coefficient than air, and thus is more efficient in cooling. In order to take advantage of the higher heat transfer coefficient, it is necessary that the s team b e pure, which requires measurement of ions, typically anions, at levels less than 1 ppb, or in the ppt range.

Ion chromatography is typically used for ion measurement. U.S. Pat. Nos. 5,908,556; 5,597,481; 4,981,804; and 4,766,550 exemplify the prior art for ion chromatography; these patents are incorporated herein by reference in their entirety for all purposes. In power plants, demineralized water is used for making steam. Steam purity is obtained by consolidation of the contaminants in the steam drum and subsequently controlled by blowdown. An on-line sampling system and an ion chromatography system are preferred for frequent analysis of the steam that is used for cooling the turbine transition section. An on-line ion chromatography system for continuous, automated operation is commercially available, but successful validation of the results can be problematic at low ppt levels.

There remains a need in the art for an on-line chromatography system for continuous automated operation which can accurately measure ions present in concentrations less than 1 ppb.

BRIEF SUMMARY OF THE INVENTION

This invention relates to an analytical apparatus for measuring a low concentration of a constituent in a stream at a parts per billion level. The apparatus comprises: (a) a sample loop having a predetermined volume for receiving a sample from the stream, wherein the sample loop has an inlet for receiving a sample from the stream, an outlet, and a valve for switching between sample intake and sample discharge. The apparatus further comprises: (b) a purifier for producing a substantially pure carrier liquid from a sample of the stream, (c) a first multi-path valve connected to the purifier and to the sample loop for alternately connecting the loop with a sample to be analyzed and a purified carrier liquid from the purifier, (d) a preconcentrator column in fluid connection with the outlet of the sample loop for absorbing and increasing the concentration of the low concentration constituent, (e) a second multi-path valve connected to the preconcentrator column for alternately connecting the column with the carrier liquid containing the constituent and with an eluent for the constituent, (f) a source of an eluent for the constituent, the source being connected to the second multi-path valve, and (g) a detector in fluid connection with the preconcentrator column for receiving and analyzing a constituent concentration in an eluent received from the preconcentrator column.

The invention also includes a method of analyzing a stream for a low concentration constituent present in the stream at a parts per billion level. The method comprises the steps of: (a) introducing a first sample from the stream into a sample loop having a predetermined volume for containing a predetermined volume of the first sample, so as to fill the loop with the first sample; (b) purifying a second sample of the stream to produce substantially pure carrier liquid; (c) and injecting the first sample into a preconcentrator column by forcing the first sample from the sample loop using the pure carrier liquid for absorbing and increasing the concentration of the low concentration constituent on the preconcentrator column. The method further comprises: (d) introducing an eluent into the preconcentrator column to transport an absorbed constituent from the preconcentrator column to a detector; and (e) analyzing the eluent for a concentration of the constituent therein.

The invention also provides a method of on-line calibration of an analytical apparatus for measuring a low concentration of a constituent in a stream at a parts per billion level, comprising the steps of: (a) introducing a first sample from a standard stream comprising a known low concentration of a known constituent into a standard loop having a predetermined volume for containing a predetermined volume of the first sample, so as to fill the loop with the first sample; (b) purifying a second sample of the standard stream to produce substantially pure carrier liquid; (c) injecting the first sample into a preconcentrator column by forcing the first sample from the standard loop using the pure carrier liquid for absorbing and increasing the concentration of the low concentration constituent on the preconcentrator column; and (d) introducing an eluent into the preconcentrator column to transport an absorbed constituent from the preconcentrator column to a detector. The method further comprises: (e) analyzing the eluent for a concentrator of the constituent therein; (f) calculating an amount of constituent to reach the detector; and (g) determining a calibration constant for the detector.

Finally, the invention relates to an on-line method for creating a calibration curve for a detector in an analytic apparatus for measuring a low concentration of a constituent in a stream at a parts per billion level. The method comprises the steps of: (a) introducing a first sample from a standard stream comprising a known low concentration of a known constituent into a standard loop having a predetermined volume for containing a predetermined volume of the fist sample, so as to fill the loop with the first sample; (b) purifying a second sample of the standard stream to produce substantially pure carrier liquid; (c) injecting the first sample into a preconcentrator column by forcing the first sample from the standard loop using the pure carrier liquid for absorbing and increasing the concentration of the low concentration constituent on the preconcentrator column; (d) introducing an eluent into the preconcentrator column to transport an absorbed constituent from the preconcentrator column to a detector; and (e) analyzing the eluent for a concentrator of the constituent therein. The method further comprises: (f) calculating an amount of constituent to reach the detector and (g) determining a first calibration constant for the detector. The method next comprises (h) repeating steps (a) through (c) twice in succession; (i) repeating steps (d) through (f); and j) calculating a second calibration constant for the detector. Finally, the method comprises the steps of: (k) repeating steps (a) through (c) three times in succession; (l) repeating steps (d) through (f); (m) calculating a third calibration constant for the detector; and (n) combining the first and the second and the third calibration constants to create a calibration curve for the detector.

BRIEF DESCRIPTION OF SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIGS. 2–9 are schematic diagrams showing various flow paths in an ion chromatography system according to the present invention. In FIG. 2, the sample is being loaded into the sample loop while the standard loop is being flushed. In FIG. 3, the purified carrier liquid is being used to transport the sample from the loop to the preconcentrator. In FIG. 4, the preconcentrator is injecting the sample onto the anion column while the sample lines are being flushed with carrier liquid. In FIG. 5, standard is being loaded into the standard loop. In FIG. 6, the preconcentrator is being loaded from the standard loop, using purified carrier to transport the standard and to flush the standard loop. In FIG. 7, the sample is being used to flush the sample loop, while the standard is being loaded onto the preconcentrator column. In FIG. 8, a manually initiated grab sample is being loading into the sample loop. In FIG. 9, the grab sample is being transported from the sample loop to the preconcentrator using the purified carrier.

DETAILED DESCRIPTION OF THE INVENTION

This invention includes an analytical apparatus for measuring a low concentration of a constituent in a stream at a parts per billion level. In a preferred embodiment, the stream is an aqueous stream. As used herein, "constituent" refers to any ionic content which is present in a stream. The constituent may be present in ionic or non-ionic form. If the constituent is in ionic form, the apparatus may be referred to as an ion chromatograph, which will be described in further detail below in conjunction with the drawings.

The apparatus includes a flow path designed to allow continuous on-line operation, and controls are provided to operate the equipment as if it were designed as an on-line system. This includes the ability to run samples, standards, blanks, single point calibration checks and other functions from a simple operator interface. Analog outputs are available for trending results to remote devices such as a power plant distributed control system (DCS). An optional enclosure allows the unit to be located outdoors or in other harsh environments.

A calibration methodology allows highly accurate, low-level calibration equivalent to the level of interest, less then 1 parts per billion (ppb) and specifically as low as 250 parts per trillion (ppt). Calibration at less than 250 ppt is possible with minor modifications.

The analytical apparatus is capable of reliably determining a low concentration of a constituent in a sample, in which the sample contains less than about 50 ppb of the pertinent constituent, particularly less than or equal to about 1 ppb, and more particularly in the range of from about 10 to about 1000 ppt.

The apparatus comprises at least a sample loop, a purifier, a first and a second multi-path valve, a preconcentrator column and a detector. As will be described in further detail below, an eluent flushes the constituent from the preconcentrator column into the detector. In one embodiment, the apparatus further comprises a suppressor column in fluid connection with the preconcentrator column and the detector. The suppressor column functions to remove the effect of the eluent from the detector.

In one embodiment, the stream comprises more than one low concentration constituent, and the apparatus may further comprise a separator column for separating the more than one constituent. If the apparatus is an ion chromatograph, the separator column may be an ion column, which may be in particular a cation column or an anion column.

The apparatus comprises a sample loop having a predetermined volume for receiving a sample from the stream. The sample loop comprises a first multi-path valve for switching between sample inlet and sample discharge. It is preferred if the multi-path valve comprises at least six ports. The apparatus further comprises a purifier. A portion of a sample stream is recirculated multiple times through the purifier in order to produce a substantially pure carrier liquid that is virtually free of constituents. It is preferred if the purifier is a mixed bed exchange cartridge. The first multi-path valve is connected to the purifier and to the sample loop for alternately connecting the loop with a sample to be analyzed and with a purified carrier liquid from the purifier. The outlet of the sample loop is in fluid connection with the preconcentrator column, which captures all of the constituents in the sample. The substantially pure carrier liquid is used to push the sample, which has a predetermined volume defined by the sample loop, through the preconcentrator column. The preconcentrator column also functions to increase the concentration of the constituent in the sample. The preconcentrator column can be any standard commercially available column suitable for the type of analysis.

A second multi-path valve, preferably comprising at least six ports, is connected to the preconcentrator column for alternately connecting the column with the substantially pure carrier liquid containing the constituent and with an eluent for the constituent. The source of the eluent is connected to the second multi-path valve. The eluent is preferably a solution (or mixture) of a salt or weak acid such as, for example, $NaHCO_3$, $Na_2CO_3$, or phthalic acid. Preferably, the eluent is an aqueous solution. The eluent passes through the preconcentrator column, removing all constituents from the column, and carrying the constituents to the detector. The detector, which is in fluid connection with the preconcentrator column, analyzes the concentrator of the constituent in the eluent. In a preferred embodiment, the detector is an electric conductivity detector.

A method is provided for analyzing a stream for a low concentration constituent present in the stream at a parts per billion level. As discussed above, the constituent in the stream to be analyzed may be present in ionic. The method comprises the steps of: (a) introducing a first sample from the stream into the sample loop so as to fill the loop with the first sample; (b) purifying a second sample of the stream to produce substantially pure carrier liquid; and (c) injecting the first sample into the preconcentrator column by forcing the first sample from the sample loop using the pure carrier liquid. The method further comprises: (d) introducing the eluent into the preconcentrator column to transport the absorbed constituent from the preconcentrator column to the detector; and (e) analyzing the eluent for a concentration of the constituent therein. One particular use of this method is for analyzing constituents in condensed stream.

In one embodiment of this invention, the apparatus further comprises a standard loop having a predetermined volume for receiving a sample from a standard stream comprising a known low concentration of a known constituent. The volume of the standard loop is preferably less than the volume of the sample loop, and is preferably a known multiple difference less. This difference is preferably, but need not be, a difference of 1000 in volume. For example, the standard loop may contain 10 $\mu l$ while the sample loop may contain 10 ml. The standard loop has an inlet for receiving a sample from the standard solution and an outlet.

The standard loop also comprises a third multi-path valve (which preferably comprises at least six ports) for switching between standard intake and standard discharge. The valve functions to alternately connect the standard loop with the standard sample to be analyzed with substantially pure carrier liquid from the purifier. Ultra-pure carrier liquid, purified from the sample or standard stream, is used to push the standard solution out of the standard loop and into the preconcentrator column. Thus, a known volume having a known concentration of a constituent is passed through the preconcentrator column, which captures all of the constituents of interest. Although this system may be used for other types of detectors and analyzers, when the system is an ion chromatograph, eluent is used to sweep the ions from the preconcentrator column to the ion column and from there into the detector for measurement.

This measurement on the standard solution is used to calibrate the detector. By repeating this process, the amount of ions swept into the detector can be doubled, which provides a second calibration point that is twice that of the first calibration point. The sequence may be repeated for providing a third calibration point that is three times the amount of the first calibration point. Thus, a linear calibration curve may be created for calibrating the detector.

Thus, an on-line calibration method is provided, which allows calibration of the detector without contamination caused by manual injection of the standard. Further, the detector may be calibrated for a range within its normal sensitivity, but is also capable of accurately measuring ions from a sample having a concentration of ions less than or equal to 1 ppb because a large sample volume is concentrated in the preconcentrator, which captures all of the ions in the large sample. Thus, a sufficiently high count of ions is available for measurement by the detector.

The sample and the calibration standard are each transported to the preconcentrator column by the carrier liquid. The carrier liquid is virtually free of contamination because it is repeatedly passed through a purifier, preferably a mixed bed exchange column, that removes contaminants. Thus, although the sample or standard stream itself is used, it is cleaned by this recirculation process to the point that it is virtually free of contamination and suitable for use as a carrier liquid. Separate pumps for the carrier fluid and for introducing the sample provide a stable system for carrying sample and standard to the preconcentrator column.

In one embodiment, a computerized control system is provided for switching the position of the selectors in the various multi-path selector valves for proper timing in introducing the sample or standard to the preconcentrator column. The control system includes software designed to communicate with the analytical apparatus software, and which controls the operation of the analytical apparatus by selecting the sample type to be run, reporting the results on a display, sending the results to remote computers, and reporting errors in calibration, concentration or system operation.

Figure 1:
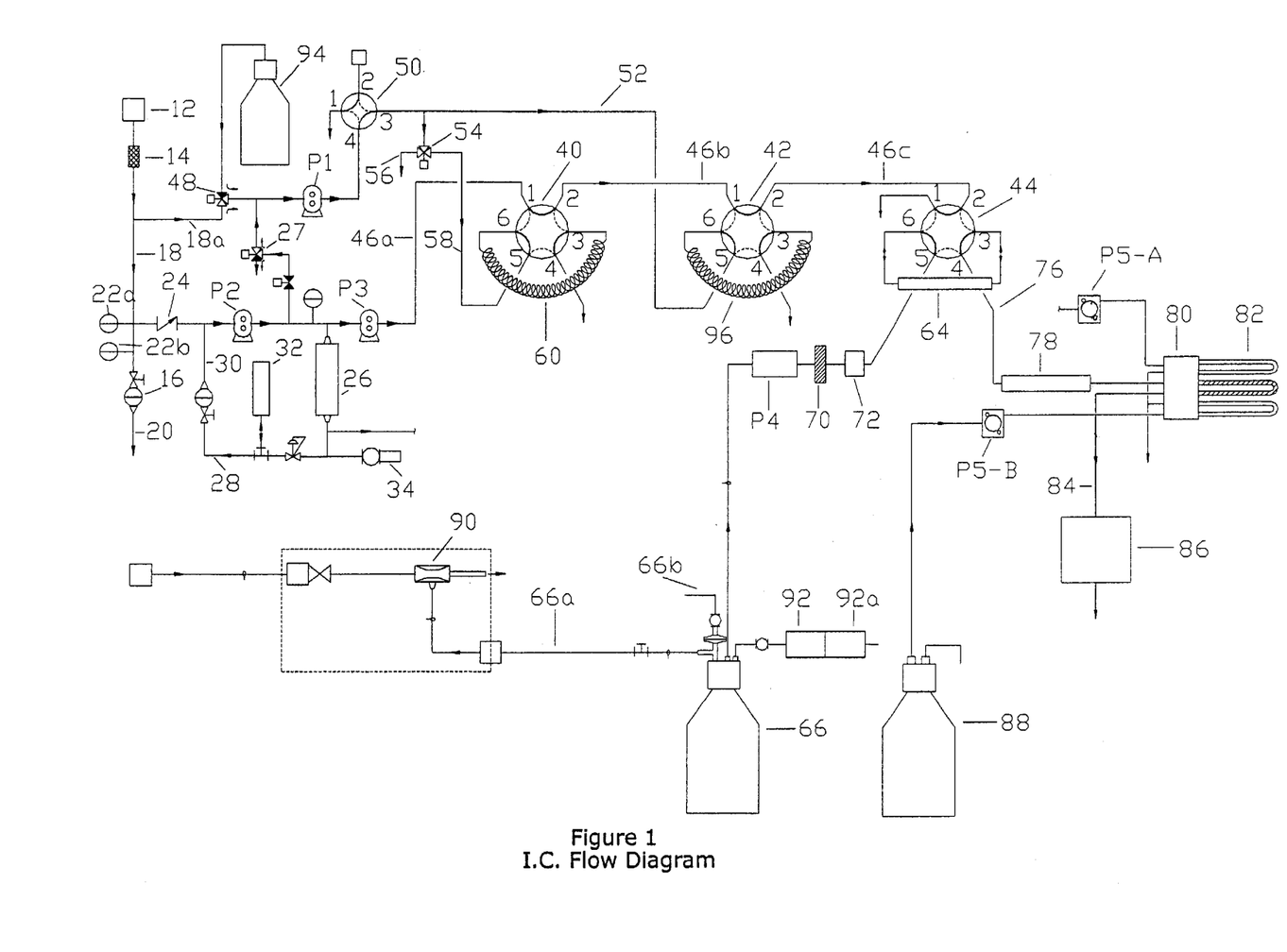
FIG. 1 is a schematic diagram of an ion chromatography system according to the present invention.
Figure 2:
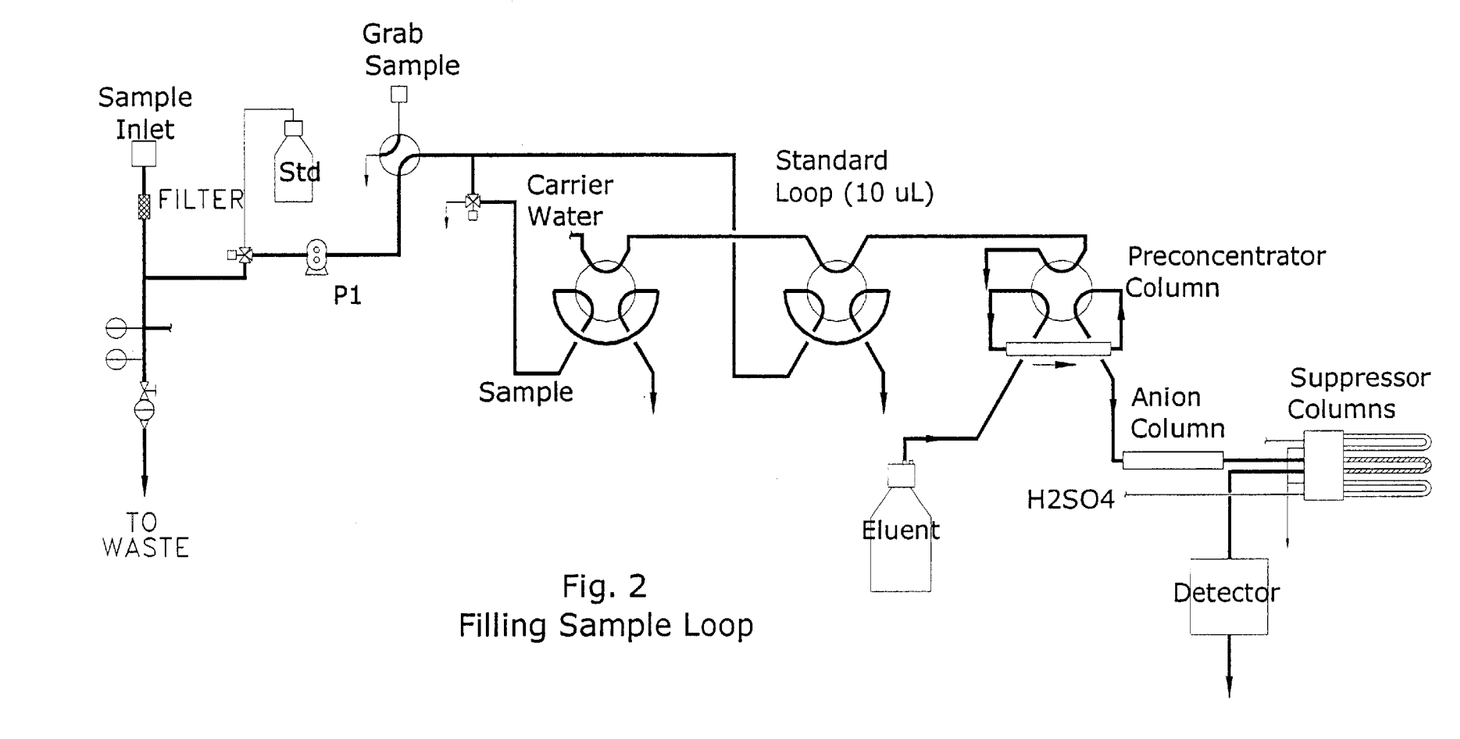
Figure 3:
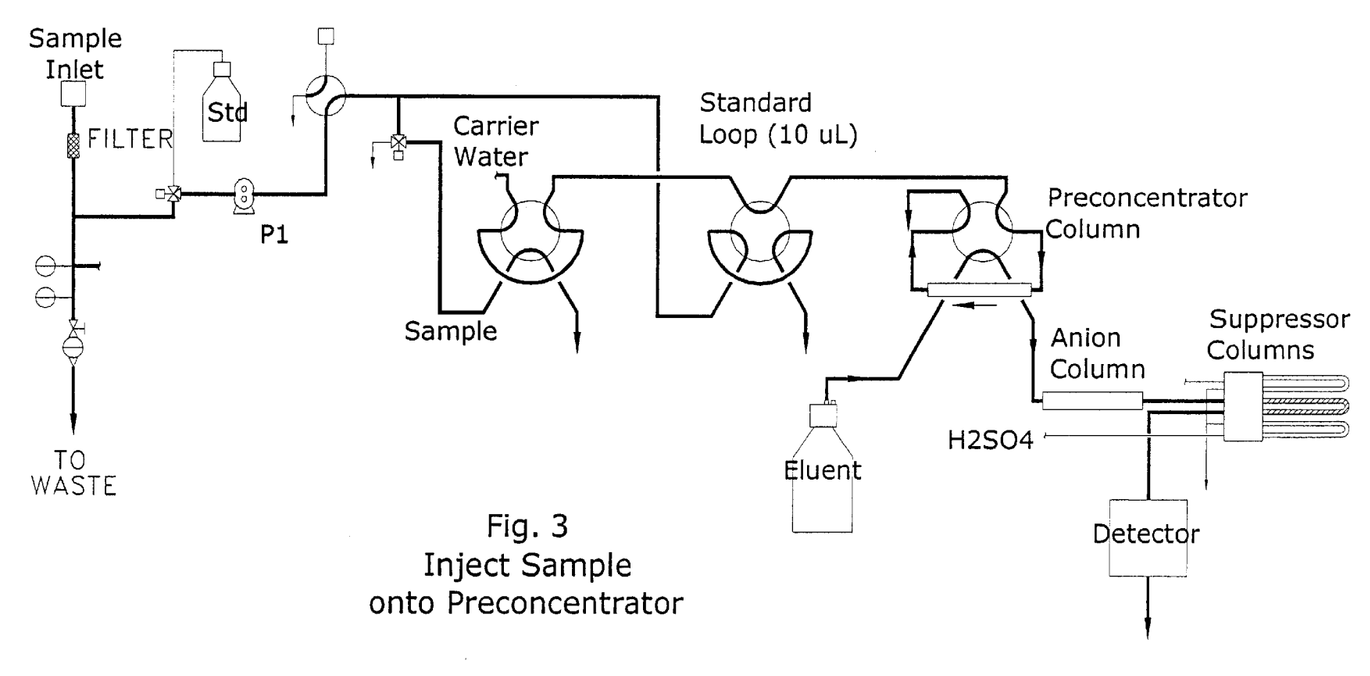
Figure 4:
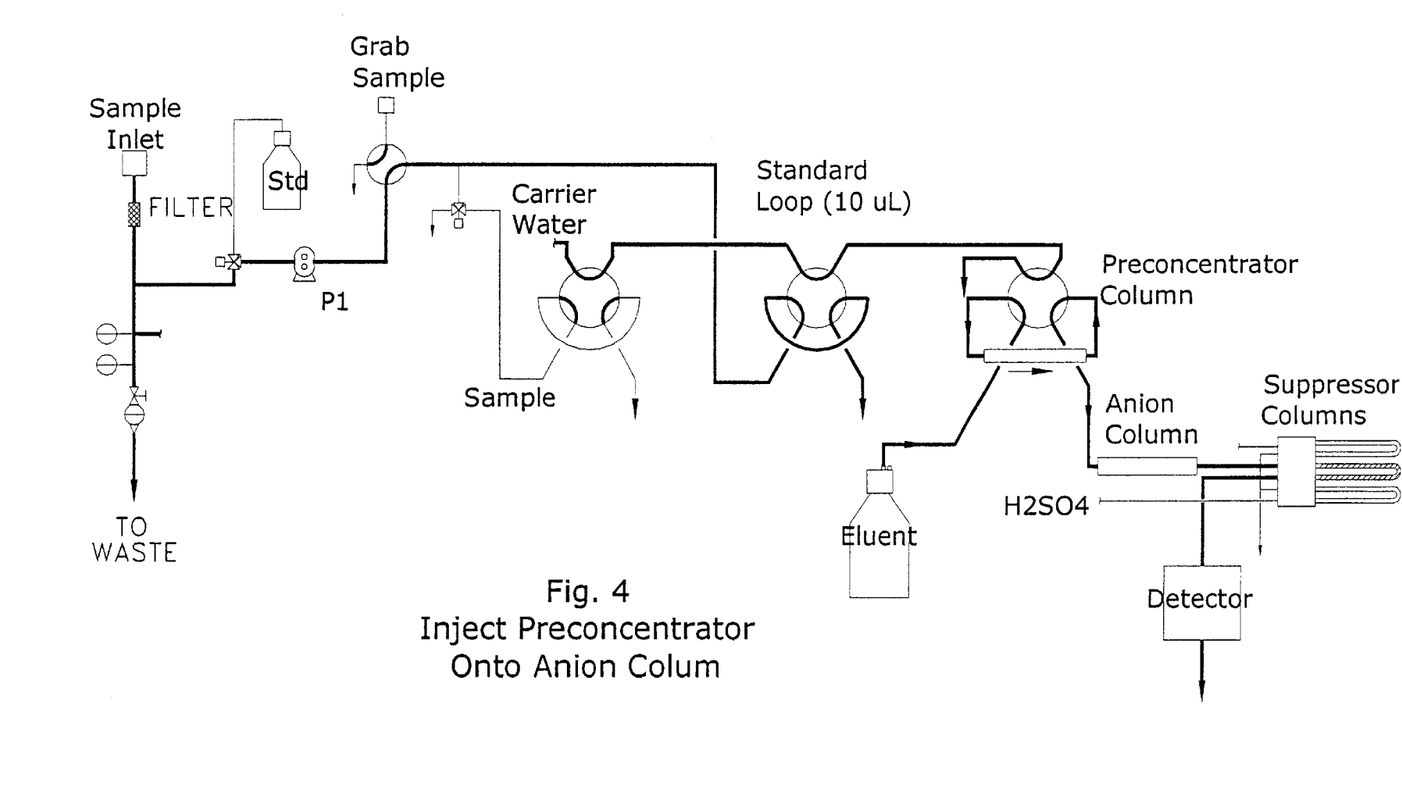
Figure 5:
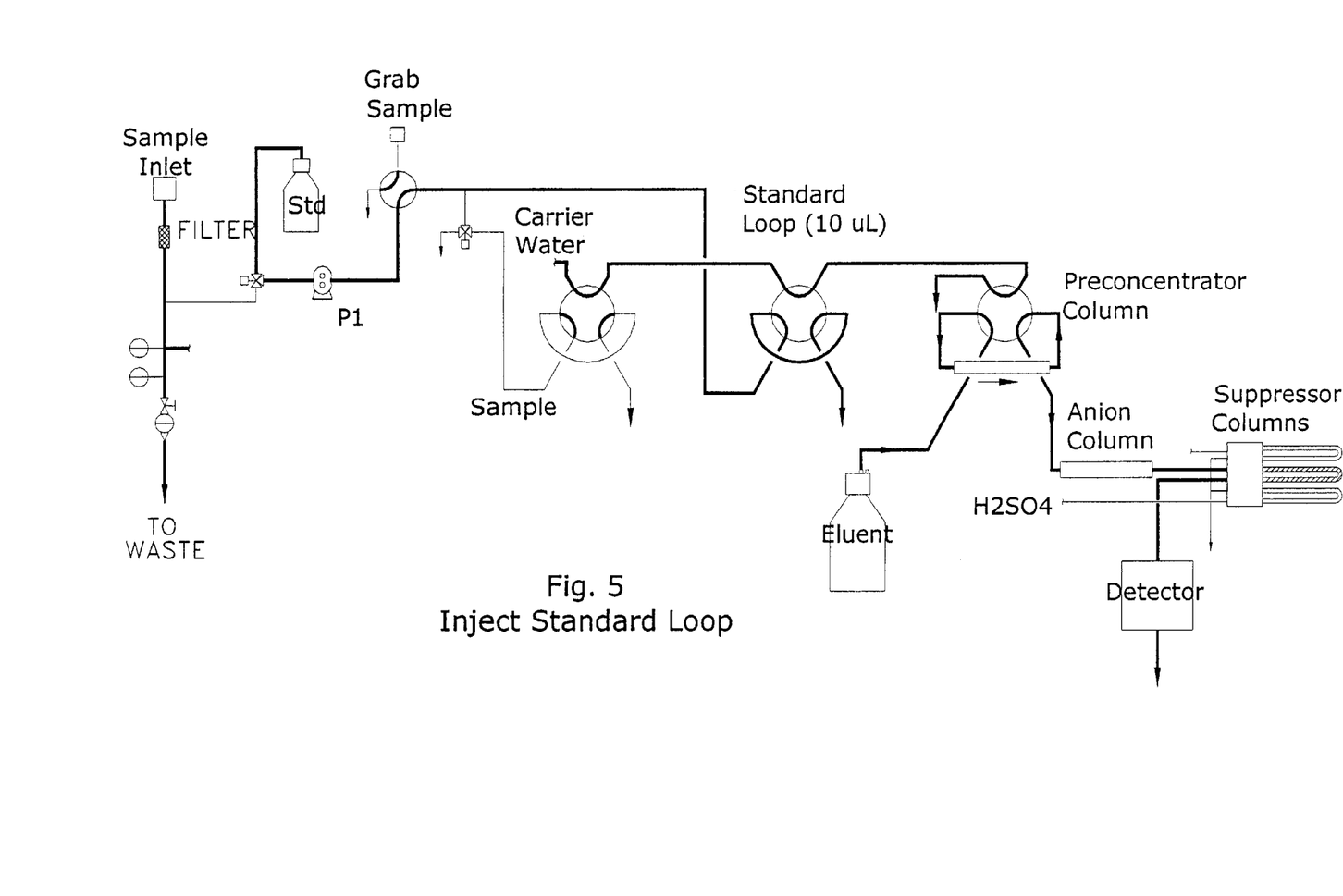
Figure 6:
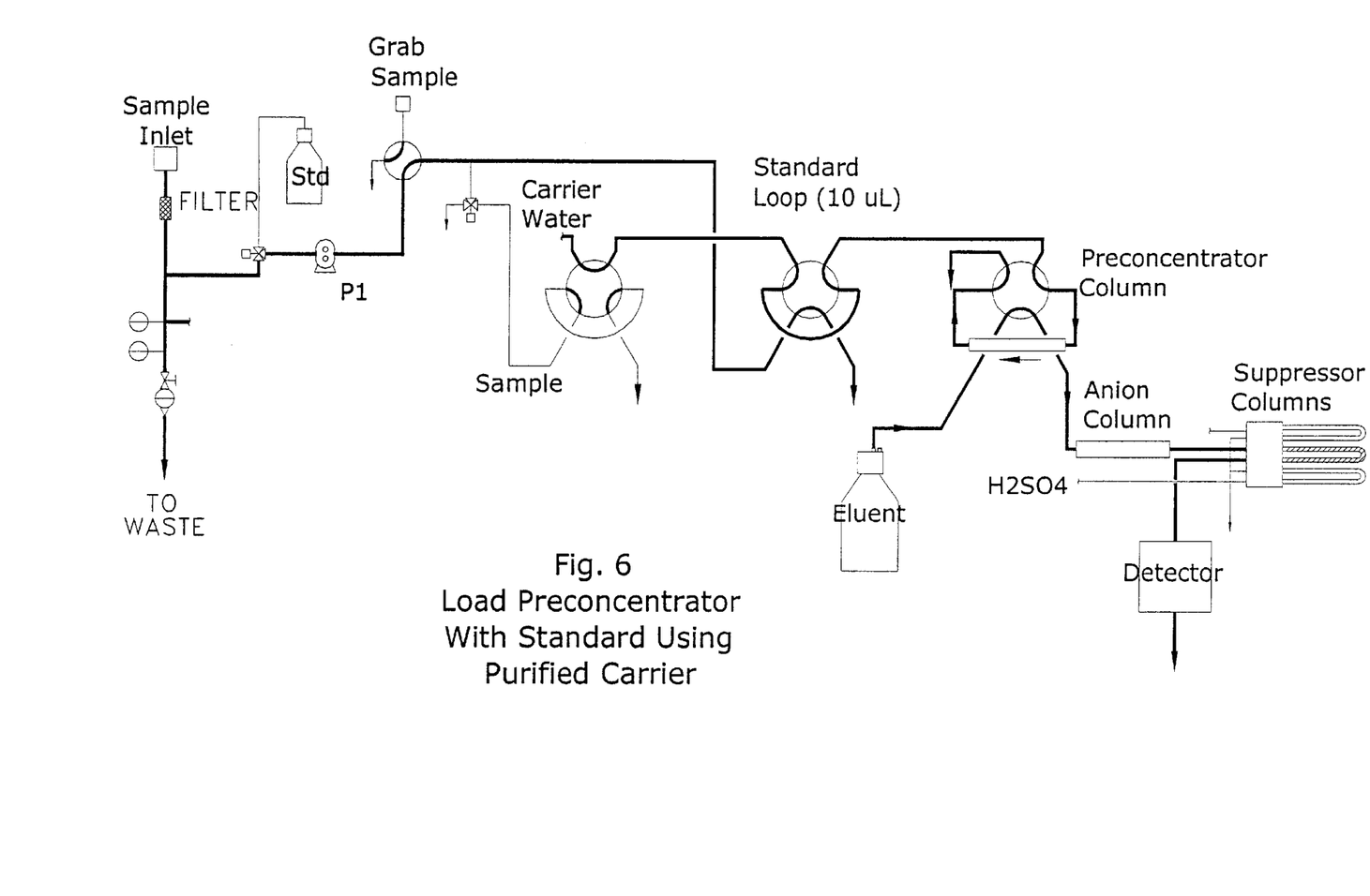
Figure 7:
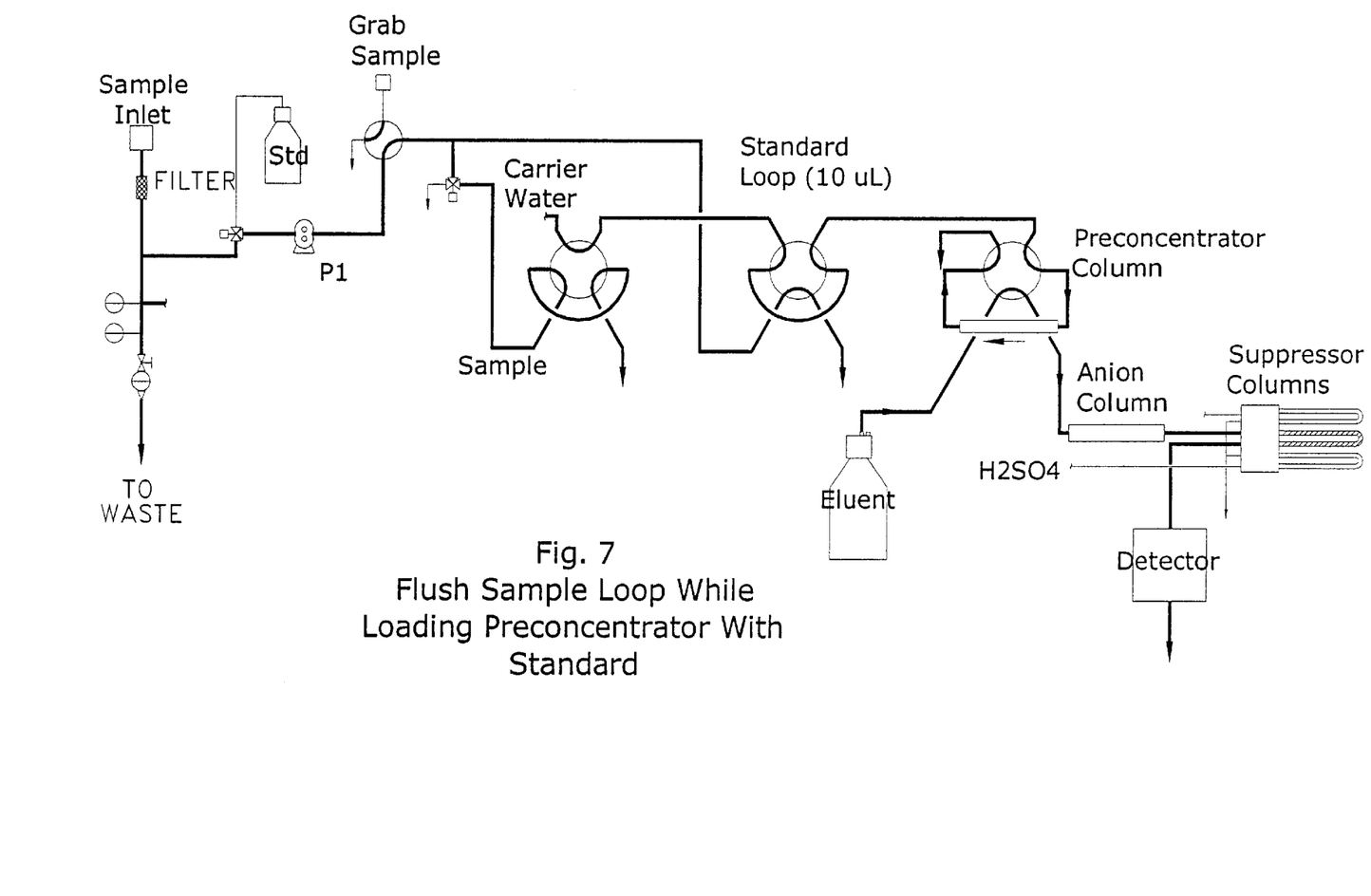
Figure 8:
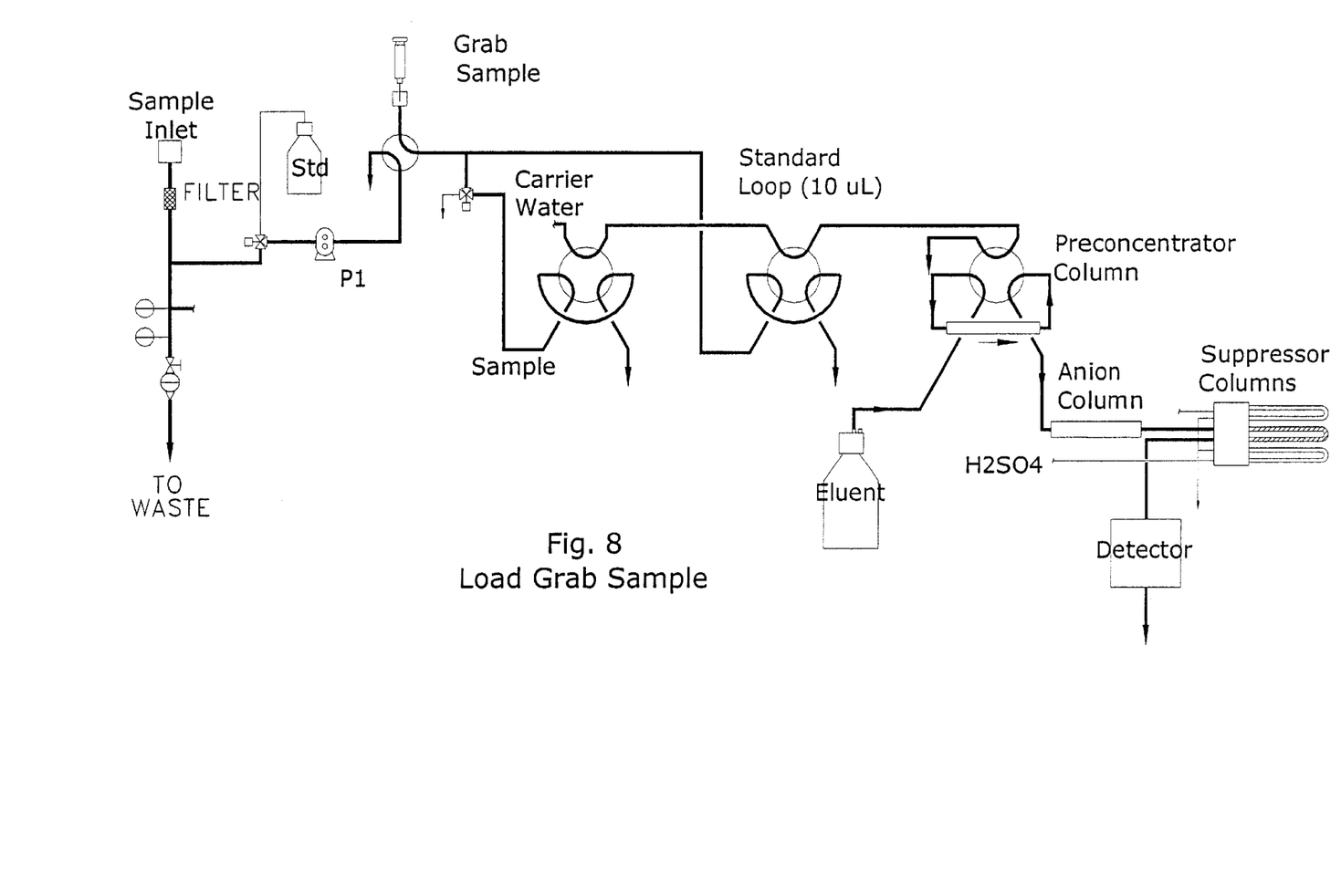
Figure 9:
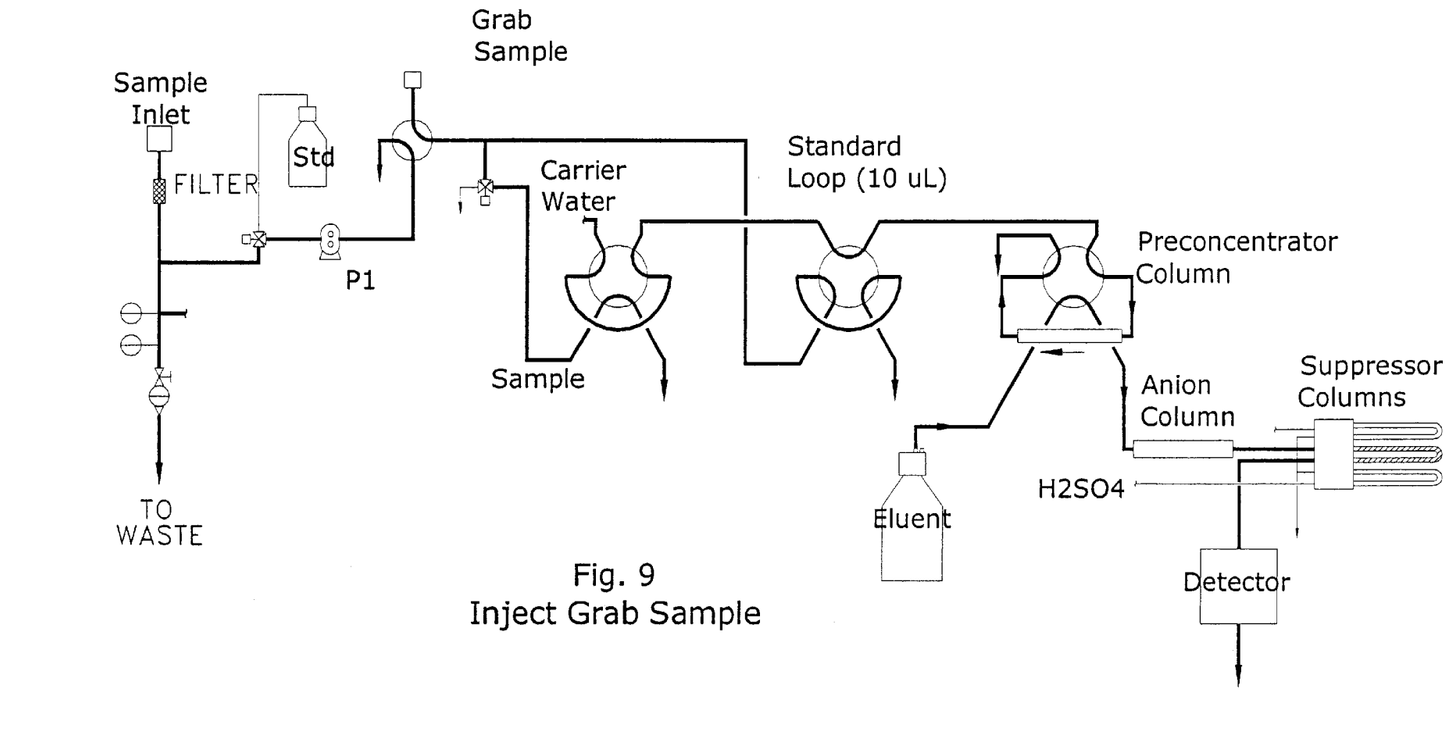

In one preferred embodiment, the analytical apparatus is an ion chromatograph, as discussed above. As shown in FIG. 1, an ion chromatograph 10 is illustrated schematically according to the present invention. The terms "ion chromatography" will be referred to herein as "IC." IC 10 is adapted for continuous, automated operation, which may be implemented by using computers, software, programmable logic controllers, microprocessors, and similar electronic-based controllers and coding. IC 10 may be used, for example, in analyzing an ion concentration in condensed steam requiring high purity for use in a turbine in an electrical power plant. However, the present invention is not limited to this application or even to an ion chromatograph as is explained further below.

Turning to FIG. 1, a sample is introduced at a sample inlet 12 and passed through a filter 14. A valve 16 is used to regulate the flow and provide a back pressure on a line 18. The flow setpoint is established based on the sample inlet size. This flow rate is maintained such that the fraction of the sample flowing into pump P2 is always representative of the current sample. This is preferred since the subsequent flow rates required for analysis are not sufficient in volume to keep the line purged with current sample. A portion of the sample is dumped to waste, typically a drain, through a line 20. Pressure transmitter 22a and pressure gauge 22b provide a pressure indication at various points in line 18.

A portion of the sample is drawn through a check valve 24 into the suction of a pump P2, which is preferably a gear pump although other pump types, such as peristaltic, can be used. The sample is circulated through a mixed bed exchange cartridge 26 and through a line 28 back to the suction of pump P2. This recirculation process provides a source of virtually pure blank carrier liquid for sample and standard transport. Mixed bed exchange cartridge 26 purifies what was originally a part of the sample, providing an ultra-pure carrier for transporting a sample as explained further below.

A recirculation loop 30 is configured to pass fluid through mixed bed exchange cartridge 26 as many times as is necessary to remove any contaminant in the fluid, which may typically be as many as 50 passes. The pure liquid is used to fill a storage tank 32, for use as a backup sample in the event of loss of sample at the inlet to the IC. An extraction port 34 is provided for extracting a grab sample of the ultra-pure water for independent verification. The flow rate in the circulation loop 30 may be set at any flow rate desired, such as between about 25 and about 500 cubic centimeters (cc) per minute, preferably at about 150 cc per minute. Outflow and makeup rates are much less than the recirculation rate, ensuring ultra-high purity carrier liquid. For example, the outflow and makeup rate may be about 3 cc per minute for a recirculation flow rate of about 150 cc per minute. A back pressure regulator 27 ensures that the pump P2 discharge pressure, and subsequently pump P3 suction pressure, are maintained at a constant pressure. The flow rate through P3 can remain constant only if the suction pressure is also constant. This can not be guaranteed solely on the basis of the pump P2 discharge pressure because the pump P2 suction is subject to pressure fluctuations reflected by varying plant operational characteristics.

Ion chromatograph 10 has three six-way valves 40, 42, and 44. Each six-way valve has six ports numbered 1–6. During injection, pump P3 continuously flushes ultra-pure carrier liquid through ports 1 and 2 in the six-way valves 40, 42 and 44.

Pump P3 has a discharge line 46 that is connected to inlet line 46a for valve 40, entering port 1. Port 2 of valve 40 is connected to port 1 of valve 42 using line 46b, and port 2 of valve 42 is connected to port 2 of valve 44 using line 46c. The pure carrier liquid from pump P3, by proper selection of the switching valve position, may be used to push the liquid in the sample loop 60 or the standard loop 96 to the preconcentrator column 64, or alternatively may be used to flush valves 40, 42 and 44. Thus, virtually pure carrier liquid may be delivered to six-way valves 40, 42 and 44 on a continuous basis during operation. The carrier liquid is virtually pure, although it originated from the sample, because it was thoroughly cleaned in recirculation loop 30 by multiple passes through mixed bed exchange cartridge 26, which removed all ions from the sample liquid. Note: the previous change is significant because it's a major basis of the patent.

A sample of liquid possibly containing constituents (i.e. an on-line sample) is drawn into pump P1 through line 18a and through a three-way valve 48. Pump P1 discharges to a diverting valve 50. As illustrated, the sample is discharged from pump P1 into port 4 of diverting valve 50, which is a four-way valve. To provide grab sample analysis, diverting valve 50 may be rotated so that the sample flows into port 4 and discharges through port 1 to waste through valve 50. Alternatively, the grab sample may be injected into port 2 and out port 3. In this configuration, the grab sample would continue on the same path as a normal sample as described below.

Valve 50 normally connects port 1 with port 2 and port 3 with port 4. Sample flows into port 4 and discharges through port 3 into line 52. Part of the flow passes through port 5 of the six-way valve 42, out port 6, through standard loop 96, into port 3, out port 4, and to drain. Sample also flows to a three-way valve 54, which may be set to pass the liquid to waste through a line 56 or to port 5 of six-way valve 40 through line 58. With valve 54 set properly, sample flows from line 52 through valve 54 into line 58 and into port 5 of six-way valve 40.

Sample flows into port 5 of valve 40 and discharges through port 6 into a sample loop 60. Sample loop 60 is adapted to hold a particular volume, the purpose of which will become apparent with the explanation below. In this example, sample loop 60 is adapted to hold precisely 10 milliliters (ml), although other volumes may be used depending on the application. Sample discharges from port 6 through sample loop 60 and into port 3, where it is illustrated as discharging to waste through port 4.

By changing a selector position on six-way valve 40, the flow between the ports may be changed to that indicated by the dashed line. Thus, fluid communication is established between ports 1 and 6; between ports 2 and 3; and between ports 4 and 5. Upon switching the selector to place port 1 in fluid communication with port 6, virtually pure carrier liquid flows from pump P3 through line 46a into port 1 and discharges through port 6. The carrier liquid pushes the sample out of sample loop 60 into port 3 and out through port 2 into line 46b.

IC 10 is preferably automatically controlled so that a selector on six-way valve 44 is rotated in its position when the selector for valve 40 is rotated in its position. Consequently, sample is pushed by carrier liquid from line 46b, through valve 42 ports 1 and 2, through line 46c and into valve 44 port 2 for discharge through port 3 into a preconcentrator column 64. The sample is pushed through preconcentrator column 64 into port 6 for discharge through port 1 to waste. Preconcentrator column 64 operates to trap all ions in the sample in column 64 so that the liquid passed to waste through port 1 is virtually free of any ions.

In this case, a known volume of sample, namely 10 ml in this example, has been passed through preconcentrator column 64. For concentration of ions in preconcentrator column 64, the sample in sample loop 60 may be pushed to column 64 as many times as desired, which concentrates the ions to a level that can be satisfactorily measured, as explained further. Preferably, sample loop 60 is large enough, in this case 10 ml, so that a single sample volume has sufficient ions for detection.

To measure ions captured in preconcentrator column 64, the selector for six-way valve 44 is changed to place port 5 in fluid communication with port 6. In this manner, an eluent, such as $NaHCO_3$ or $Na_2CO_3$, from container 66 can be drawn through a line 68 to eluent pump P4. Fluent pump P4 discharges through a filter 70 and through a pulse dampener 72 into a line 74, which flows into port 5 of six-way valve 44. The eluent discharges through port 6 of valve 44 into preconcentrator column 64. The eluent picks up and carries or pushes ions within the preconcentrator 64 into port 3 and out of port 4 of valve 44. The eluent pushes ions from preconcentrator column 64 into line 76 and into an ion column 78.

Thus, a concentrated sample is pushed or carried by the eluent from column 64 into ion column 78 where the anions show an affinity for a resin that is packed into anion column 78. The anions become separated into constituent chemical species, determined by valence and molecular weight of the ions. In this example, an anion column is illustrated, but a cation column may be used alternatively to anion column 78.

For anions, anion column 78 separates, for example, the following anions: fluoride, chloride, bromide, nitrite, nitrate, phosphate and sulfate. As is known in the art, the eluent solution carries the sample through anion column 78 into a switching valve 80, then through a suppressor column 82 and into a line 84 to a detector 86. For cation analysis, different commercially available columns may be used for separation, which typically resolve such cations as lithium, sodium, ammonium, potassium, calcium and magnesium.

Although various detectors may be used, for measurement of ions, detector 86 is preferably an electrical conductivity detector which provides an electrical signal proportional to the concentration of a particular anion (or cation or other species, depending on the application). Thus, a distinct peak is provided for each constituent species in the sample, and the area under a curve for that species is proportional to the count or amount of that species in the sample. The final determination for measurement of a contaminant in the sample, in this case ions, is measured as ions per unit volume, such as ions per cubic centimeter (cc).

To regenerate the suppressor column, a suppressant, such as an acid, is fed to suppressor column 82 through switching valve 80 by a peristaltic pump P5B from a container 88. Pure carrier liquid from the mixed bed exchange cartridge flows to pump P5A and then the suppressor switching valve 80, where it flushes the sulfuric acid solution from the regenerated suppressor column 82.

The eluent in container 66 should not be contaminated. To fill container 66 while minimizing contamination, a vacuum is drawn on line 66a by an eductor 90 so that eluent is drawn into container 66 through a line 66b. Compressed air is preferably used through eductor 90 to create a slight vacuum in line 66a. $CO_2$ scrubbers 92 may be used to prevent the formation of carbonic acid in the eluent, and water absorbers 92a may be used to prevent contamination of the $CO_2$ absorber and prevent absorbed water from affecting the eluent concentration.

Detector 86 is an electrical conductivity detector, which has a minimum level of detectability of about 50 ppb without suppression. However, the anion concentration in the sample at inlet 12 is a mere fraction of 1 ppb. The use of preconcentrator column 64 thus allows for an increase in contaminant concentration to a level that is measurable by detector 86. However, detector 86 should be calibrated in order to accurately measure contaminants at such a low concentration level.

In the prior art, a detector was calibrated by manually injecting a calibration standard. However, at a concentration level of less than 1 ppb, manual calibration is unsuitable because contamination may be introduced to the system through a manual injection process. Further, a calibration standard solution having a contaminant concentration in a range of 1 ppb is not readily available, where the preconcentrator column 64 could be used as a contaminant multiplier, because a standard at such a low concentration level is not stable. Thus, the standard at such a low concentration level cannot be relied on for having ions at the stated concentration. However, it is desirable, if not necessary, to calibrate the system at levels closer to the 1 ppb level, for which calibration standards are not available.

In other commercially available systems, calibration may be accomplished by injection of a concentrated standard into a flowing steam or injection into a batch for creation of low-level standards. In the present invention, an on-line calibration method is provided that eliminates the manual injection process and provides a calibration range below 1 ppb. Yet, the calibration solution contains the species to be measured at a concentration high enough to exceed the minimum level of detectability by detector 86. The concentration of the constituent in the calibration standard is also sufficiently high to provide concentration stability. This is accomplished by a volumetric manipulation between the sample and the standard.

Volumetric manipulation is possible since the final unit of measurement for ions is a count of the number of ions per unit of volume of a sample fluid. An ion count is a count of the number of ions in a sample, which remains the same even if the sample is diluted or concentrated. Thus, the ion count for 250 ppb of the ion in a 10 microliter sample is the same as the ion count for 250 ppt if the solution diluted to a volume of 10 milliliters using a pure diluent. Based on this concept, a calibration system according to the present invention is now described.

Ion chromatograph 10 is calibrated as follows. A standard having a suitable concentration of a suitable constituent is placed in container 94. The concentration illustrated in FIG. 1 is 250 ppb of an anion, as an example. It is important to note that although the measurement level is desired at below 1 ppb, a standard of 250 ppb is used. The standard is withdrawn from container 94 through three-way valve 48 into pump P1. With the diverting valve 50 in an appropriate position, pump PI discharges the standard into port 4 and out through port 3 into line 52. A small portion of the standard is discharged through three-way valve 54 via line 56. Line 56 is a 20 microliter tube designed to provide greater back pressure than the standard loop 96. However, a major portion of the standard is passed into port 5 of six-way valve 42.

The standard flows into port 5 of valve 42 and out through port 6 into a loop 96 for holding a predetermined volume of standard solution and port 6 discharges into port 3 through port 4 for discharge as waste. Standard loop 96 has a predetermined volume that is related to the volume of sample loop 60 in a particular way. In this illustration, standard loop 96 has a volume of 10 microliters while sample loop 60 has a volume of 10 milliliters. Thus, the sample loop 60 has a volume that is 1,000 times greater than the volume of the standard loop 96.

The standard solution in standard loop 96 must be transported into preconcentrator column 64. Mixed bed exchange cartridge 26 and recirculation loop 30 provide a source of virtually pure blank carrier liquid for transporting the standard into preconcentrator column 64. Although the sample from sample inlet 12 contains likely at least a magnitude lower concentration level of the contaminate than is in standard container 94, the sample could be used to transport the standard in standard loop 96 into the preconcentrator column 64, but the use of purified carrier liquid as the means of transport is preferable. The highly purified carrier liquid from recirculation loop 30 via pump P3 is used to transport the standard solution in loop 96 to the preconcentrator 64. Mixed bed exchange cartridge 26 and recirculation loop 30 provide a source of virtually pure blank carrier liquid for transporting the standard into preconcentrator column 64.

A selector in six-way valve 42 is turned so that virtually pure carrier liquid is introduced to port 1 for passage through port 6 into standard loop 96. The standard is then pushed out of standard loop 96 through port 3 out of port 2 into line 46c. The standard flows from line 46c into port 2 of six-way valve 44 and through port 3 into preconcentrator column 64, which captures all the ions from the standard. The amount or count of ions in the standard is known since the volume of standard 96 is fixed.

Ions from the standard are captured or trapped in preconcentrator column 64, and the carrier liquid pushes the standard solution out to a drain via ports 6 and 1 of six-way valve 44.

Ions trapped in preconcentrator column 64 from standard loop 96 are passed to anion column 78 and detector 86 for calibrating detector 86. Eluent from container 66 is introduced to port 5 of six-way valve 44 using pump P4. The eluent discharges through port 6 and into preconcentrator column 64, where the eluent displaces the ions and transports them via line 76 to anion column 78. The anions in the standard from container 94 (or any suitable constituent to be used for calibrating detector 86) pass through anion column 78 through switching valve 80, through suppressor column 82 and into detector 86 through line 84. Since the standard in container 94 had a known concentration of the anion that is detected by detector 86, and since standard loop 96 had a known volume, the ion count for the standard introduced at detector 86 is known. Thus, detector 86 can be properly calibrated and a method for single-point calibration is provided.

However, a multi-point calibration is desirable as it improves the accuracy of the calibration curve generated for detector 86. This can be accomplished with the present invention by repeating the standard preconcentration sequence, which when repeated twice provides a standard concentration in preconcentrator 64 that is doubled. This measurement provides a second calibration point.

Similarly, repeating the sequence three times generates a sample point representing a triple concentration equivalent. This is possible because the carrier fluid from pump P3 and recirculation loop 30 is virtually free of contaminants. To repeat the standard loop sequence twice, standard loop 96 is filled a first time with the standard solution from container 94. The standard is then pushed through preconcentrator column 64 as described above using virtually pure carrier liquid from pump P3. Standard loop 96 is filled again with the standard from container 94, and this volume is again pushed from standard loop 96 to preconcentrator column 64 using clean carrier liquid.

Eluent is then used to displace ions from the standards that are now trapped in preconcentrator column 64 and to transport them to anion column 78 and detector 86, which produces a response twice that of a single volume of standard loop 96. A triple concentration is similarly obtained by repeating this sequence again to provide a third volume of standard from standard loop 96 to preconcentrator column 64, where ions in the standard are then pushed by the eluent into anion column 78 and detector 86.

Two data points provide a better calibration curve than a single data point, but three data points are even more preferred. With three data points available, a linear equation may be generated with significantly greater reliability than that generated with a single-point calibration. With a single-point calibration, errors for offset cannot be evaluated as the curve is generated from the point through the origin. With an independent line equation, however, the y-intercept may be evaluated. If the distance is significantly large, an alarm may be generated for alerting an operator to inspect the system.

Extrapolation of data at the very lowest levels of measurement may not be considered reliable, and extrapolation from a single-point calibration may introduce a significant source of error. However, a three-point calibration that passes through the origin is likely to provide a calibration for detector 86 that is reliable. Consequently, data may be extrapolated to other points on the calibration line. Thus, a calibration system is provided for calibrating detector 86 within a range of sensitivity that is within current technological capabilities. A standard may be used that is stable and at a sufficiently high concentration range for satisfactorily calibrating detector 86.

On the other hand, a contaminant level in a sample may be measured when the contaminate level is one, two or three levels of magnitude less than that in the standard. This is possible because, in this case, the volume of sample loop 60 is 1,000 times greater than the volume of standard loop 96. Since the preconcentrator column 64 captures all ions in a sample or in the standard, without regard to concentration, a total ion count may be determined by detector 86 with suitable calculations. Thus, detector 86, which is suitable for detection of ions above about 50 ppb, may also be used for measuring ions in a sample at a concentration of less than about 1 ppb due to the volumetric manipulations described above.

The volume of standard loop 96 has been illustrated here as 10 $\mu$l and the sample loop as 10 ml. However, these volumes may be adapted as required for the particular application, changing both the absolute volume as well as the relationship or ratio of the volumes. Thus, the volumetric manipulation is adaptable to the particular application.

The use of sample to create ultra-pure liquid suitable for use as a carrier allows more accurate results unaffected by minor changes in flow rate. For example, if an injection device is used to create a low level standard, the concentration of the resultant standard is affected by the accuracy of the injection device and the diluent volume. This directly affects the calibration. In the present invention, the standard loop has a precisely known volume which is unaffected by normal "wear and tear", and the use of ultra-pure carrier liquid, coupled with timing of valve switching, guarantees that the standard is at, or very close to, the expected concentration. Due to the high purity of the carrier liquid, minor fluctuations in the flow rate will not significantly affect the results.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of on-line calibration of an analytical apparatus for measuring a low concentration of a constituent in a stream at a parts per billion level, comprising the steps of:
    (a) introducing a first sample from a standard stream comprising a known low concentration of a known constituent into a standard loop having a predetermined volume for containing a predetermined volume of the first sample, so as to fill the loop with the first sample;
    (b) purifying a second sample of the standard stream to produce substantially pure carrier liquid;
    (c) injecting the first sample into a preconcentrator column by forcing the first sample from the standard loop using the substantially pure carrier liquid for absorbing and increasing the concentration of the low concentration constituent on the preconcentrator column;
    (d) introducing an eluent into the preconcentrator column to transport an absorbed constituent from the preconcentrator column to a detector;
    (e) analyzing the eluent for a concentration of the constituent therein;

(f) calculating an amount of constituent to reach the detector; and (g) determining a calibration constant for the detector.

2. The method according to claim 1, wherein the apparatus is capable of measuring a low concentration constituent at a level of about 10 parts per trillion to about 50 parts per billion.

3. The method according to claim 1, wherein the apparatus comprises a flow path designed to allow continuous on-line operation, by creating a continuously flowing sample and carrier liquid.

4. The method according to claim 1, wherein the apparatus is adaptable for continuous, automated operation.

5. The method according to claim 1, wherein the detector is an electrical conductivity detector.

6. The method according to claim 1, wherein the apparatus is an ion chromatograph.

7. The method according to claim 1, wherein the stream is an aqueous stream and the substantially pure carrier liquid is substantially pure carrier water.

8. The method according to claim 1, wherein the constituent is in ionic form.

9. The method according to claim 1, wherein the known low concentration of the known constituent is about 250 parts per billion.

10. The method according to claim 1, wherein the stream is condensed steam.

11. An on-line method for creating a calibration curve for a detector in an analytic apparatus for measuring a low concentration of a constituent in a stream at a parts per billion level, comprising the steps of:

(a) introducing a first sample from a standard stream comprising a known low concentration of a known constituent into a standard loop having a predetermined volume for containing a predetermined volume of the first sample, so as to fill the loop with the first sample;

(b) purifying a second sample of the standard stream to produce substantially pure carrier liquid;

(c) injecting the first sample into a preconcentrator column by forcing the first sample from the standard loop using the substantially pure carrier liquid for absorbing and increasing the concentration of the low concentration constituent on the preconcentrator column;

(d) introducing an eluent into the preconcentrator column to transport an absorbed constituent from the preconcentrator column to a detector;

(e) analyzing the eluent for a concentration of the constituent therein;

(f) calculating an amount of constituent to reach the detector;

(g) determining a first calibration constant for the detector;

(h) repeating steps (a) through (c) twice in succession;

(i) repeating steps (d) through (f);

(j) calculating a second calibration constant for the detector;

(k) repeating steps (a) through (c) three times in succession;

(l) repeating steps (d) through (f);

(m) calculating a third calibration constant for the detector; and (n) combining the first and the second and the third calibration constants to create a calibration curve for the detector.

12. The method according to claim 11, wherein the apparatus is capable of measuring a low concentration constituent at a level of about 10 parts per trillion to about 50 parts per billion.

13. The method according to claim 11, wherein the apparatus comprises a flow path designed to allow continuous on-line operation, by creating a continuously flowing sample and carrier liquid.

14. The method according to claim 11, wherein the apparatus is adaptable for continuous, automated operation.

15. The method according to claim 11, wherein the detector is an electrical conductivity detector.

16. The method according to claim 11, wherein the apparatus is an ion chromatograph.

17. The method according to claim 11, wherein the stream is an aqueous stream and the substantially pure carrier liquid is substantially pure carrier water.

18. The method according to claim 11, wherein the constituent is in ionic form.

19. The method according to claim 11, wherein the known low concentration of the known constituent is about 250 parts per billion.

20. The method according to claim 11, wherein the stream is condensed steam.

* * * * *